United States Patent [19]

Stevens

[11] Patent Number: 4,923,462
[45] Date of Patent: May 8, 1990

[54] CATHETER SYSTEM HAVING A SMALL DIAMETER ROTATABLE DRIVE MEMBER

[75] Inventor: Robert C. Stevens, Williston, Fla.

[73] Assignee: Cordis Corporation, Miami, Fla.

[21] Appl. No.: 233,998

[22] Filed: Aug. 15, 1988

Related U.S. Application Data

[63] Continuation of Ser. No. 27,186, Mar. 17, 1987, abandoned.

[51] Int. Cl.⁵ ............................................. A61B 17/32
[52] U.S. Cl. ................................. 606/159; 606/180; 604/22
[58] Field of Search ............................ 604/22, 27, 53; 128/304, 305, 310; 606/159, 180

[56] References Cited

U.S. PATENT DOCUMENTS

| | | | |
|---|---|---|---|
| 3,525,339 | 8/1970 | Halligan . | |
| 3,614,953 | 10/1971 | Moss et al. . | |
| 3,732,858 | 5/1973 | Banko | 604/22 |
| 3,811,446 | 5/1974 | Lerwick et al. . | |
| 3,976,077 | 8/1976 | Kerfoot, Jr. | 128/305 |
| 4,445,509 | 5/1984 | Auth . | |
| 4,589,412 | 5/1986 | Kensey . | |
| 4,646,736 | 3/1987 | Auth | 128/303 R |
| 4,664,112 | 5/1987 | Kensey et al. | 128/303.11 |
| 4,686,982 | 8/1987 | Nash | 128/305 |
| 4,690,140 | 9/1987 | Mecla | 128/305 |
| 4,696,667 | 9/1987 | Masch | 128/305 |
| 4,700,705 | 11/1987 | Kensey et al. | 128/303.11 |
| 4,747,821 | 5/1988 | Kensey et al. | 604/22 |
| 4,754,755 | 7/1988 | Husted | 128/305 |
| 4,784,636 | 11/1988 | Rydell | 604/22 |
| 4,795,438 | 1/1989 | Kensey et al. | 604/22 |
| 4,798,586 | 1/1989 | Stevens | 604/22 |

FOREIGN PATENT DOCUMENTS

| | | | |
|---|---|---|---|
| 167927 | 1/1986 | European Pat. Off. | 128/305 |
| 442795 | 9/1974 | U.S.S.R. | 128/305 |
| 1235321 | 6/1971 | United Kingdom . | |
| 2093353 | 9/1982 | United Kingdom | 128/305 |

OTHER PUBLICATIONS

*Cardiovascular News*, McMahen Publishing Co., "High-RPM Rotary Blade for Angioplasty Tested" Feb. 1986 pp. 1 & 4.

*Primary Examiner*—Stephen C. Pellegrino
*Assistant Examiner*—Ralph Lewis
*Attorney, Agent, or Firm*—Watts, Hoffmann, Fisher & Heinke

[57] ABSTRACT

Method and apparatus for opening a partially or totally occluded blood vessel. A conventional catheter is inserted within a patient and the condition of a blood vessel ascertained. If it is determined that sufficient blockage exists to cannulize the vessel, a small diameter drive catheter having a rotatable head at a distal end is inserted into the conventional catheter in close proximity to the occluded region. The head is rotated at high speeds as dye is injected through the catheter to monitor progress of the procedure. Different sized rotating heads having different blockage removing characteristics are inserted until the procedure has been completed to the physician's satisfaction. The drive mechanism is a small d.c. powered hand-held motor operated by the physician during the procedure.

13 Claims, 4 Drawing Sheets

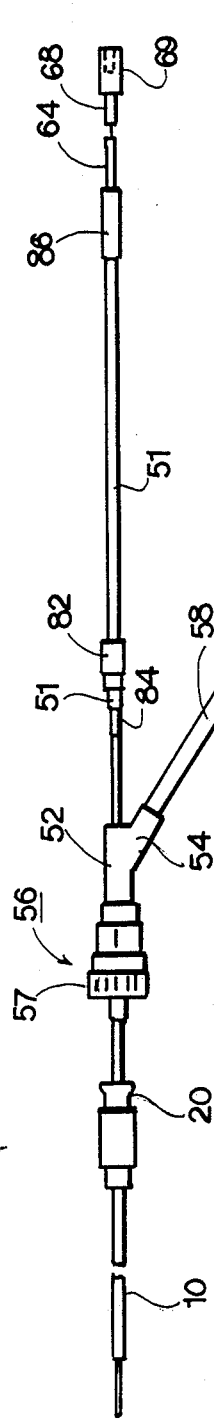
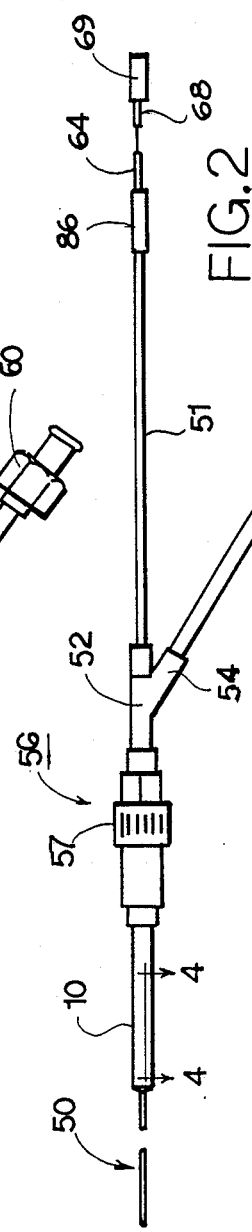
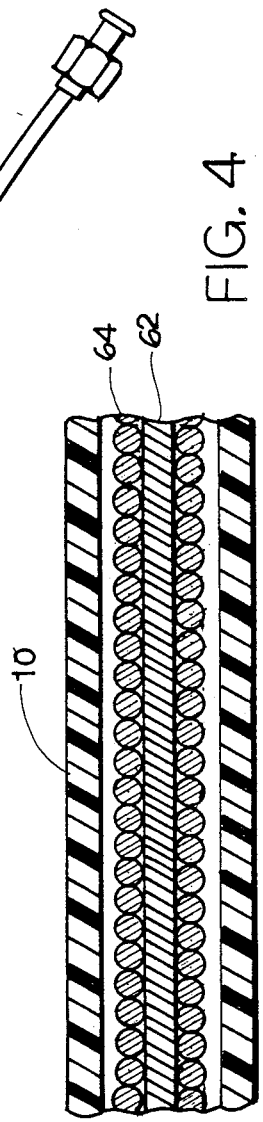

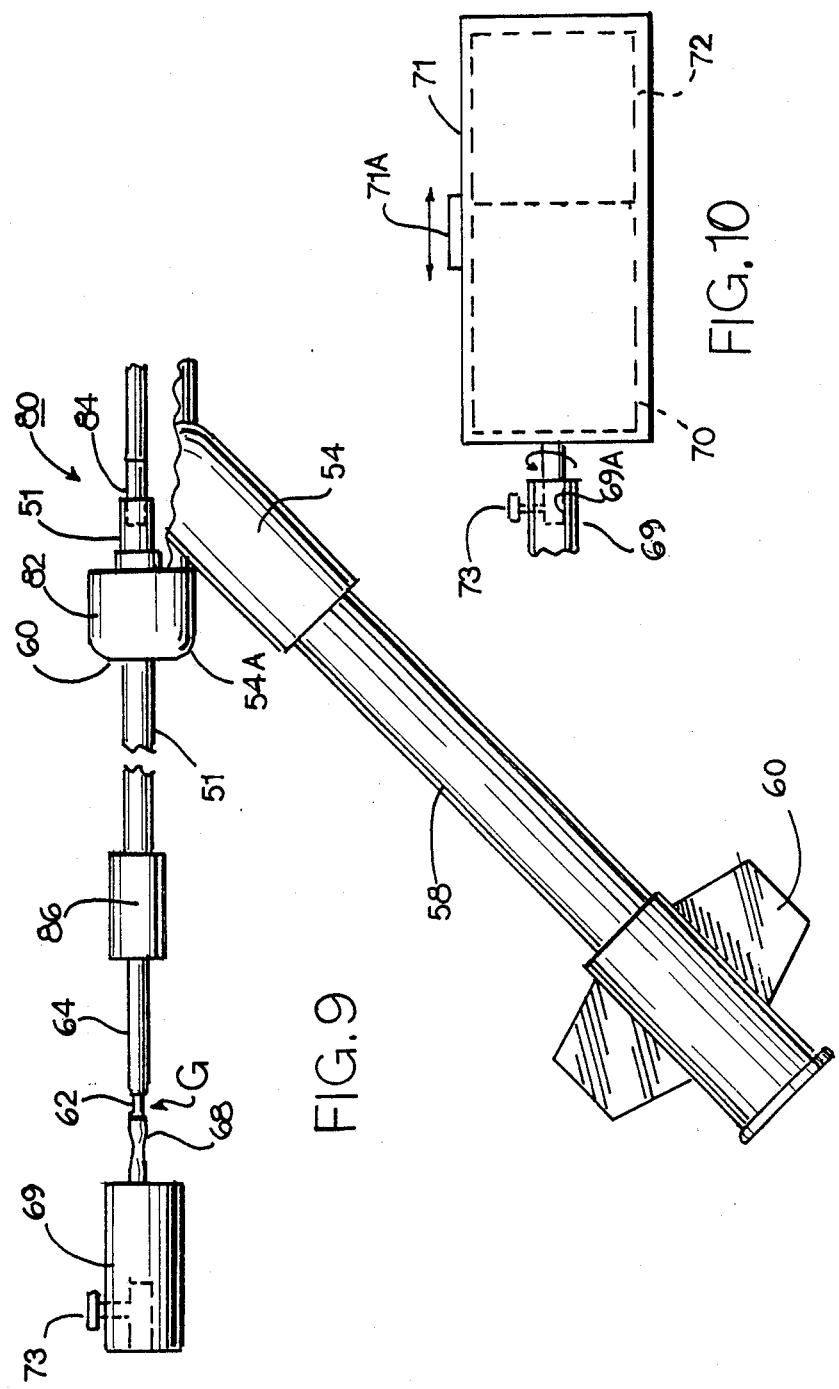

CATHETER SYSTEM HAVING A SMALL DIAMETER ROTATABLE DRIVE MEMBER

This is a continuation of co-pending application Ser. No. 07/027,186 filed on 3-17-87 now abandoned.

TECHNICAL FIELD

The present invention relates to a catheter system having a rotatable drive member for opening a totally or partially occluded blood vessel.

BACKGROUND ART

Due to a mechanism not entirely understood, a person's cardiovascular blood delivery system often becomes less efficient as one ages. Although the causes of arterioscleroris are not completely understood, one symptom is the partial or, in extreme cases, the total blockage of a blood vessel due to a build up of deposits along an inner surface of the blood vessel. The increase in the number of coronary by-pass operations is some indication of the incidence with which the problem is encountered in older patients.

Prior art proposals recognize that one possible procedure for treating a condition of partially or totally blocked blood vessels is to open the blocked blood vessel. One such prior art technique for reopening a blocked blood vessel is to insert a balloon catheter within the vessel to expand the vessel and either break loose deposits within the vessel or alternatively, increase the size of the lumen passing through those deposits.

An alternate proposal for opening a blocked vessel is to bring a high-speed rotating device into contact with occluded portions of the blood vessel. The rotating device produces cutting, abrading, or fluid turbulence to open the vessel and increase blood flow. One device for physically opening the blood vessel in this manner is disclosed in U.S. Pat. No. 3,762,416 to Moss entitled "Improvements In or Relating To Drills for Clearing Obstructions". In this patent, a high-speed motor rotates a flexible drive shaft connected to a cutting bit. The bit and flexible drive shaft are inserted into an occluded blood vessel so that when the bit is rotated at high speed and moved into contact with occluded regions it breaks loose deposits within the blood vessel.

A more recent prior art patent disclosing a similar system for blood vessel cannulization is disclosed in U.S. Pat. No. 4,445,509 to Auth entitled "Method and Apparatus for Removal of Enclosed Abnormal Deposits". This patent describes a differential cutting tool mounted at the end of a flexible shaft which can be inserted into an occluded blood vessel. Again, high speed rotation of the cutting tool causes the tool to remove abnormal deposits from inside the blood vessel.

U.S. Pat. No. 4,589,412 to Kensey entitled "Method and Apparatus for Surgically Removing Remote Deposits" discloses a procedure for removing atherosclerotic plaque. A cutting tip is rotated by the application of fluid pressure through a multi-lumen catheter.

The systems disclosed in these prior art patents include a flexible catheter having an integral rotable cutting tool for removing material within an occluded blood vessel. When the physician inserts the catheters disclosed in these prior art patents an obstructed or partially occluded blood vessel has most probably already been identified using a conventional angiographic catheter and angiographic imaging techniques. The angiographic catheter is withdrawn and one of the dedicated catheters re-inserted for treatment of the vessel obstruction.

A typical prior art angiographic system includes a metering pump for delivering an opaque dye to an angiographic catheter that has been inserted into the patient. The metering pump delivers the opaque dye at a controlled rate as the physician monitors a viewing screen to observe the internal structure of the patient. During this procedure, occluded regions of a patient's blood vessel can be identified. The angiographic catheter is then removed. One of the special catheters having an integral rotating head at its distal end might then be re-inserted to position the rotatable head in proximity with the occluded region to cannulize or open the blocked vessel.

A number of patents disclose prior art angiographic catheters. U.S. Pat. No. 3,503,385 entitled "Guidable Catheter Assembly and Manipulator Therefore", U.S. Pat. No. 3,485,234 entitled "Tubular Products and Method of Making Same", and U.S. Pat. No. 3,585,707 entitled "Method of Making Tubular Products" are representative prior art patents relating to angiographic catheters. These three patents are assigned to the assignee of the present invention and are incorporated herein by reference.

Due to the construction of the catheters disclosed in the aforementioned prior art patents to Moss, Auth and Kensey, it is anticipated the process of re-inserting the second catheter, routing it to the occluded region of the vessel and cannulizing the vessel may be difficult, especially for small diameter vessels. Indeed, it may be that the catheters proposed in these prior art patents are larger in diameter than the vessel that needs cannulization.

DISCLOSURE OF THE INVENTION

The cannulization procedures disclosed in the prior art patents mentioned above are still in a developmental stage. The present method and apparatus represent advances that may make these procedures viable alternatives to surgical bypass and balloon catheterization. Practice of the present invention will allow a physician to remove obstructions from partially or totally occluded blood vessels of much smaller diameter that is presently believed possible. In addition, the two-step procedure whereby an occluded vessel is first located and in a second procedure obstructions are removed is combined into a process that is simpler to perform and therefore entails less risk to the patient.

In accordance with the method of the invention, a catheterization process is conducted starting with the step of inserting an elongated catheter having a central passageway into a patient blood vessel. This is a standard procedure well known in the medical imaging art. As the elongated catheter is being inserted into the vessel, the physician monitors passage of the catheter since the catheter is opaque to x-radiation and can be monitored using real time imaging techniques known in the radiographic art. Once the catheter has been inserted into the patient, an opaque dye is pumped through the catheter, out the distal end, and passes into a patient blood vessel. The passage with time of the dye through the vessel is monitored to locate obstructions or regions of reduced blood flow within that blood vessel.

Once an obstructed region is located, in accordance with the present invention, the physician need not withdraw the catheter and re-insert a separate device. Instead, an elongated rotatable drive catheter having a rotatable head at one end is inserted into the central passageway of the angiographic catheter and pushed by the physician into the region of the obstruction. The rotatable head can be pushed a short distance beyond the distal end of the angiographic catheter into contact with deposits that occlude the blood vessel.

High speed rotation cannulizes or opens the vessel. As the rotating head of the drive catheter advances forward the physician also pushes the angiographic catheter toward the obstruction to guide the drive catheter. This prevents the drive catheter from "wandering" inside the blood vessel and possibly eroding healthy vessel tissue.

Another advantage achievable through practice of the invention is that the two-step process of the prior art is reduced into a single procedure where the occluded regions are identified and treated. An additional advantage is that different size or type of rotatable heads can be freely substituted, one for the other, depending upon the nature of the blood vessel and the occlusion. Since the central passageway of the catheter is not totally occupied by the drive system, passage of the opaque dye through the angiographic catheter to monitor performance of the procedure is not impeded. One additional advantage is the ability to apply suction to the catheter to remove deposits that have been dislodged by the rotating head. Alternately suction can be applied during intervals when the rotatable head is withdrawn from or pulled back inside the angiographic catheter.

The aforementioned process has been made possible through development of a narrow drive wire and bearing system for inserting the rotating head into the angiographic catheter. The drive wire is a flexible wire having a flattened rotatable head at its distal end. The drive wire is surrounded by an elongated bearing extending nearly the entire length of the drive wire. The rotating head extends from the distal end of the bearing. A bushing for coupling the drive wire to a motor for rotating the drive wire extends from a proximal end of the bearing.

The bearing comprises a tightly coiled wire that is wound around a mandrel and then coated with a synthetic covering. The bearing is then removed from the mandrel and the drive wire inserted through the bearing. The rotatable head and coupling are then attached to complete construction of the drive system. The bearing seals the drive wire from fluid inside the catheter, acts as a heat sink to absorb heat generated as the drive wire rotates inside the bearing, and facilitates passage of the drive catheter through the angiographic catheter since the synthetic coating acts as a lubricant.

The drive system length and diameter are tailored for specific applications so that depending upon the passageway defined by the angiographic catheter, a suitable drive wire and rotatable head can be pushed entirely through the catheter to the vicinity of a blocked blood vessel.

One other aspect of the invention is the mechanism for energizing the rotatable head. The coupling at the proximal end of the drive wire is attached to a d.c. powered high-speed motor that is preferably energized by a low cost, low voltage battery. Use of a low voltage d.c. energization signal is safer than potentially hazardous higher level a.c. drive voltages.

From the above it is appreciated that one object of the invention is an improved method and apparatus for opening blockages or regions of reduced blood flow in a blood vessel. This and other objects, advantages and features of the invention will become better understood from a detailed description of a preferred embodiment of the invention described in conjunction with the accompanying drawings.

BRIEF DESCRIPTION OF THE DRAWINGS

FIG. 2 is an elevation view of a proximal end of the drive catheter inserted into and connected to the proximal end of the angiographic catheter;

FIG. 3 is an exploded elevation view of proximal portions of the angiographic and drive catheters of FIG. 2;

FIG. 4 is a section view taken along the plane defined by the line 4—4 in FIG. 2;

FIG. 9 is an enlarged, partially sectioned, view of a bifurcated connector showing a seal to prevent fluid from leaking from the bifurcated connector; and FIG. 10 is a schematic representation showing a drive unit including a d.c. motor for energizing the drive catheter.

BEST MODE FOR CARRYING OUT THE INVENTION

Figure 1:
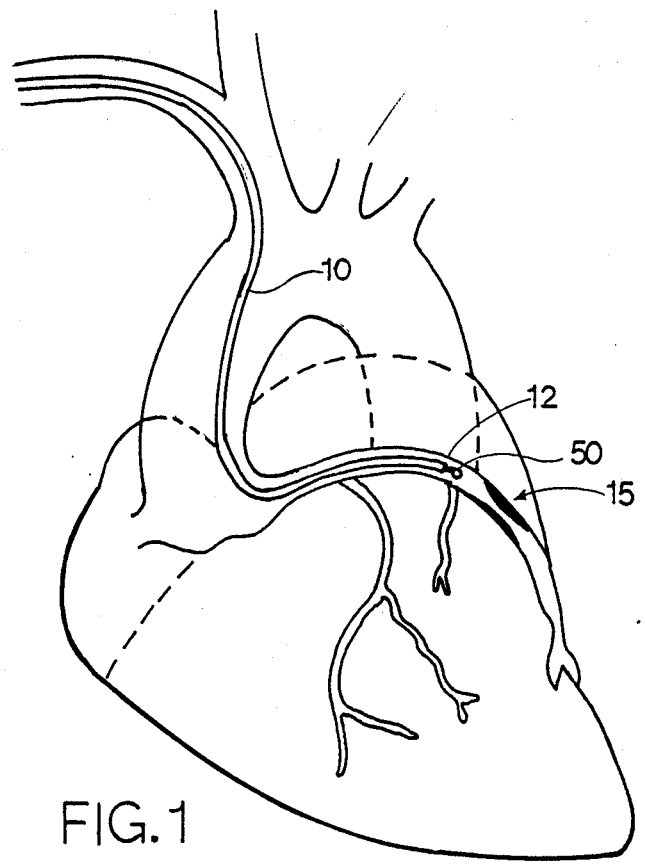
FIG. 1 is a schematic depiction showing the distal end of an angiographic catheter guiding a drive catheter into a patient's left coronary artery.

Turning now to the drawings, FIG. 1 schematically depicts an angiographic catheter 10 inserted into a patient's coronary artery 12. Various techniques are known in the medical imaging field for inserting an angiographic catheter into the coronary artery for an angiographic study. One technique, known as the Sones technique involves insertion of a catheter into a patient's brachial artery and guiding the catheter 10 into the coronary artery region. Progress of the catheter is monitored on the angiographic display since the catheter 10 is constructed in part using a radio-opaque material. Suitable Ducor (Registered Trademark) catheters are commercially available from the assignee of the invention for the Sones angiographic study.

Radio-opaque dye in high concentrations is injected into the catheter 10 through a Leur hub 20 at the catheter's proximal end (FIG. 2) and the condition of the artery diagnosed by the physician. When the angiographic study is conducted, it is anticipated that a certain number of patients will have occluded or partially occluded coronary arteries resulting in reduced blood flow to the heart. Additional details of the angiographic study of a coronary artery may be found in a number of printed publications, one of which is entitled "Coronary Arteriography and Angioplasty" by King, Spenser B. M.D. and Douglas, John S., Jr. M.D., McGraw Hill Book Company, 1985. See Chapters 6 and 7, pp. 137–217 which are incorporated herein by reference.

While the coronary artery angiographic examination is emphasized here, it is appreciated that similar techniques are utilized in the medical imaging field for examining a number of different blood vessels. The coronary artery example is chosen since the cornary artery requires a narrow catheter (French No. 3, O.D. of one millimeter (0.039 inch) or less). If the coronary artery will receive a specialized catheter constructed in accordance with the teachings of the prior art patents to Moss, Auth, and Kensey discussed above, it is believed the coronary artery by definition is not occluded.

When the physician conducting the angiographic study of the coronary artery observes a region 15 of partial blockage of the coronary artery, the present invention enables immediate treatment of that condition through insertion of a drive catheter 50 that can be directly inserted into the angiographic catheter 10 used to conduct the coronary study.

To insert the drive catheter 50 the physician disconnects an injector (syringe or the like) from the leur fitting 20, removes the drive catheter 50 from a sterilized package and inserts a distal end into the catheter 10. Before it is packaged the catheter 50 is inserted through a tube 51 coupled to a plastic bifurcated "Y" connector 52 having a side-arm branch 54 for injection of fluids. A conventional rotating adapter 56 coupled to the "Y" connector 52 has a leur fitting 57 that engages the leur hub 20 of the angiographic catheter 10. This allows the "Y" connector 52 to rotate while allowing saline/dye solutions to be injected.

Coupled to the side-arm branch 54 is a flexible tube 58 and a conventional leur fitting 60 for injecting fluid into the catheter 10. The leur fitting 60 is used for injecting controlled concentrations of opaque dye and saline solution as the blocked region of the vessel is opened.

The drive catheter 50 (FIGS. 5-8) includes a drivewire 62 rotatably mounted within a sleeve bearing 64 that passes through the in-line branch of the "Y" connector 52 as well as the adapter 56. A flattened rotating head 66 is formed at the distal end of the drivewire 62 and a drive bushing 68 is crimped onto the proximal end of the drivewire 62.

The drive catheter 50 can be constructed to have a range of diameters and utilize rotating heads 66 of different shape and size. In one embodiment, the rotating head 66 comprises a piece of stainless steel hypodermic tubing that is flattened and TIG welded at the distal end of the drivewire 62. In small diameter applications the end of the drive wire is flattened to form the rotating head.

The sleeve 64 comprises a tightly coiled wire wound on a mandrel and coated with a thin (0.002 inch) teflon coating to make the sleeve 64 impervious to fluid entry and allow the drive catheter 50 to slide through the angiographic catheter 10. Once the wire has been wound about the mandrel and coated, it is separated from the mandrel and defines a flexible tube or sheath having a center passageway suitable for receipt of the drivewire 62. The thin teflon coats the wire but does not penetrate the interior of the coil so that the coiled sleeve can be separated from the mandrel. The drivewire is inserted through the sleeve 64 and the head 66 and drive bushing 68 attached to opposite ends of the drivewire.

The drive bushing 68 is also crimped to a motor coupling 69 having an cylindrical opening 69a to accommodate the output shaft of a small drive motor 70. The motor 70 is mounted in an easily manipulated hand-held unit 71 (FIG. 10) having a switch actuator 71a and a conventional low voltage d.c. battery 72. A motor output shaft is inserted into the coupling 69 tightened by a locking screw 73 and transmits rotational motion to the drive wire 62. Rotational speeds of up to 30,000 revolutions per minute are deemed to be desirable in the procedure and commercially suitable motors having either variable speed adjustments or constant outputs are known in the art.

A seal 80 (FIG. 9) inside the connector 52 prevents the saline/dye solution that is pumped into the catheter 10 via the side-arm 54 from leaking from the connector 52. A plastic bushing 82 fits over and is fixed to the plastic tube 51 forming the in line branch leading to the connector 52. During fabrication the drive catheter 50 is pushed through the tube 51 and a teflon sleeve 84 is pressed into the tube end. The sleeve 84 is then heat treated to cause it to shrink and form a fluid seal between the tube 51 and the teflon coated sleeve 64 of the drive catheter. The plastic bushing 82 is then heat fused to the "Y" connector 52 to position the seal 80 within the connector 52. The drive catheter is then free to slide back and forth through the connector 52 but fluid injected through the side branch 54 does not leak from the connector 52.

The hand-held unit 71 and drive catheter 50 are stored in a sterilized package and are disposable so that for each procedure a new sterilized package is opened. This reduces the chances of contamination from one procedure to the next subsequent procedure. Since the drive catheter is coiled during storage a small (approx. 1/64 inch) gap G (FIG. 9) is left between the end of the sleeve 64 and the drive bushing 68. This allows the catheter to be coiled without stressing the rotating head 66 and/or bushing 68.

The preferred embodiment of the invention includes a re-inforcing sleeve 86 fixed to the tube 51 that facilitates manipulation of the angiographic catheter 10 during the procedure. The invention incorporates a metering pump (not shown) somewhat different from conventional pumps known in the angiographic imaging art. A suitable pump allows the attending physician to adjust the flow rate of the saline/dye solution injected through the catheter 10.

In a preferred embodiment of the invention a distal portion 62a (last 2-3 inches) of the drivewire 62 is machined to a reduced diameter for increased flexibility. One typical drive catheter 50 has a bearing 64 constructed of tightly wound (0.006 inch) stainless steel wire teflon coated to have a 0.025 inch outside diameter. The drivewire has a O.D. of 0.010 inch reduced at its distal end to 0.008 inch. The bushing 68 has an outside diameter of 0.042 inches and comprises a stainless steel tube crimped to the drivewire. The presently preferred motor 70 comprises an Escap model 16M 11-207 d.c. motor having a rated output of 8300 r.p.m. at 9 volts. A 24 volt battery 72 raises the maximum output speed to approximately 30,000 r.p.m.

Operation

Figure 1A:
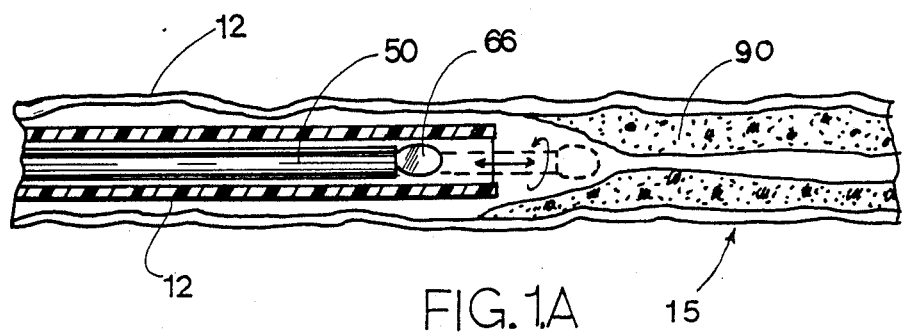
FIG. 1A is an enlarged schematic view of the drive catheter of FIG. 1 engaging a blocked region of the coronary artery.
Figure 5:
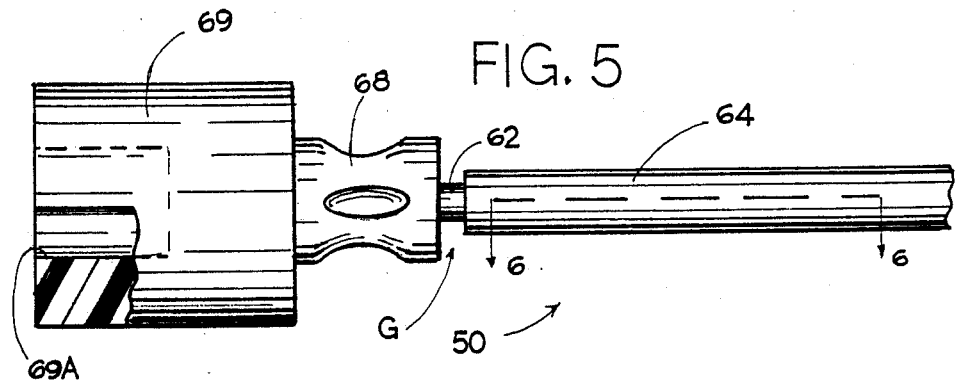
FIG. 5 is an enlarged elevation view of the proximal end of the drive catheter showing a motor coupling for transmitting a drive force to the catheter.
Figure 6:
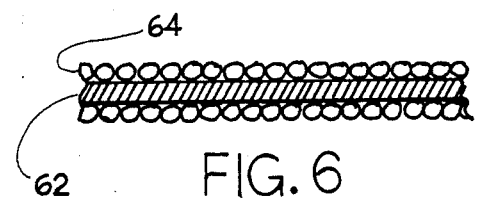
FIG. 6 is a section view as seen from the plane defined by the line 6—6 in FIG. 5.
Figure 7:
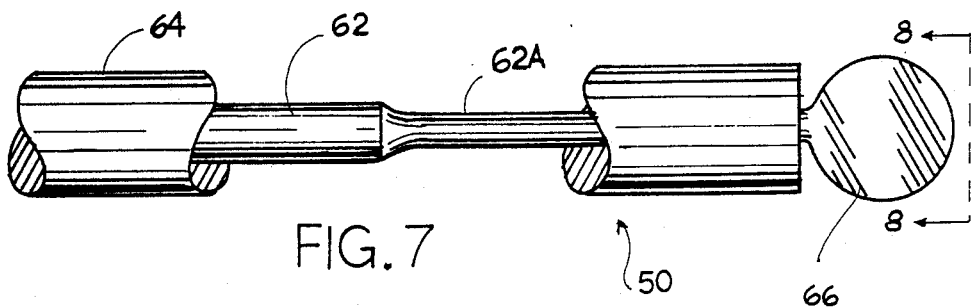
FIG. 7 is an enlarged side elevation view of the distal end of the drive catheter.
Figure 8:
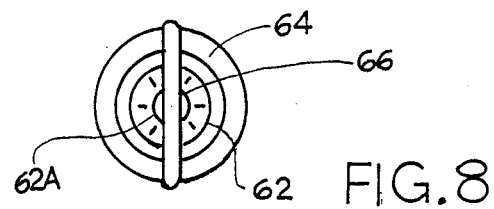
FIG. 8 is an end elevation view showing the distal end of the FIG. 7 drive catheter.

A coronary artery 12 (or other blood vessel) having deposits 90 identified during an angiographic procedure is schematically depicted in FIG. 1A. The catheter 10 is positioned next to an entry way to the deposits 90 and the drive catheter 50 inserted until the rotatable head 66 approaches the distal end of the catheter 10. The physician activates the switch 71a, which may be an on/off switch but more typically comprises a variable speed adjustment. High speed rotation of the head 66 produces fluid turbulence. The head 66 is also pushed into direct contact with the deposits 90 to produce cutting or abrading. As the process progresses, the catheter 10 can be repositioned, the flow rate of dye pumped into the catheter 10 adjusted, and the speed of rotation changed. Suction may be applied to remove dislodged deposits and other size drive catheters 50 substituted. Since the process of removing deposits with a high speed rotating device is a developing procedure, many combinations and permutations of these steps may ultimately be used to most effectively open a blocked vessel.

The present invention has been described with a degree of particularity. Alterations in the disclosed dimensions and method steps are anticipated as the process develops and it is the intent that the invention include all modifications or alterations from the disclosed method and apparatus falling within the spirit or scope of the appended claims.

I claim:

1. A process for opening a partially or totally blocked blood vessel within a subject comprising the steps of:
   inserting an elongated angiographic catheter into a subject blood vessel;
   injecting an opaque dye into a proximal end of the angiographic catheter to cause said opaque dye to flow through a central passageway of said angiographic catheter and enter the blood vessel;
   imaging the patient to locate obstructions or regions of reduced blood flow within the blood vessel which can be detected due to the presence of the opaque dye within the blood vessel;
   providing a drive catheter by rotatably supporting an elongated flexible drive wire having an enlarged distal head at one end within a tightly coiled wire having adjacent coils that touch and extend along a substantial length of said drive wire to form a sheath that acts as a bearing for the drive wire;
   without withdrawing the angiographic catheter from the patient blood vessel inserting the distal head of the drive catheter into a proximal end of the central passageway of said angiographic catheter and pushing the drive catheter into the center passageway of the angiographic catheter until said enlarged distal head is in proximity to an obstruction or region of reduced blood flow within the blood vessel; and
   rotating said drive wire at high speed relative said coiled wire sheath bearing by rotating a proximal end of the drive wire not covered by the sheath to effect high speed rotation of the enlarged distal head for opening said blood vessel.

2. The process of claim 1 wherein in addition to rotating the distal head at high speed, suction is applied at a proximal end of the elongated catheter to remove material separated from the blood vessel either during or after high speed rotation of the rotatable head.

3. The process of claim 1 wherein the opaque dye and saline is injected during high speed rotation of the head and the patient is imaged during said high speed rotation to observe the blocked region of the blood vessel.

4. The process of claim 1 wherein multiple elongated rotatable drives are inserted having differing dimensions during the process.

5. The process of claim 1 wherein as the distal head is rotated at high speed it is brought into physical contact with the obstructions or regions of reduced blood flow and the angiographic catheter is inserted along the vessel to guide the distal drive as the rotatable head opens said obstructions.

6. A catheter system for opening an obstruction in a blood vessel comprising:
   (a) a drive catheter including a distal tip for engaging the obstruction, a drive shaft coupled to the tip and an elongated sleeve supporting the drive shaft for rotation relative the elongated sleeve and having an outer surface coated with a synthetic material to facilitate insertion of the drive catheter into a diagnostic catheter, and
   (b) connector apparatus for directing the drive catheter and a fluid dye through the diagnostic catheter to the region of the obstruction including:
   (i) branch connector means having a connector body including first and second input openings in communication with an output opening, said branch connector means for routing a fluid dye from one input opening through the output opening and routing the drive catheter from the second input opening through the output opening;
   (ii) coupling means for coupling the branch connector means to the diagnostic catheter with the output opening of said connector body opening into said diagnostic catheter for routing said drive catheter and fluid into the diagnostic catheter; and
   (iii) seal means coupled to the branch connector means for inhibiting the fluid dye entering the first input opening from exiting the second input opening along an outside surface of the elongated sleeve of the drive catheter, the seal means comprising a heat shrinkable plastic tube that sealingly engages the drive catheter sleeve at the second input opening to the connector body while allowing sliding movement to the drive catheter through said connector body to allow positioning of the distal tip relative to the branch connector means.

7. A process for dislodging obstructing matter from within a subject organ comprising the steps of:
   inserting an elongated diagnostic catheter having a central passageway into a subject organ;
   injecting an opaque dye through the central passageway of said diagnostic catheter into the organ while imaging the patient to isolate said matter within the organ;
   rotatably supporting a solid, elongated flexible drive shaft, having an enlarged distal head at one end within a helically wound coiled wire sheath bearing having adjacent coils that touch and which extend along a substantial length of said flexible drive shaft;
   without withdrawing the diagnostic catheter from the organ inserting the enlarged distal head into a proximal end of the central passageway of said diagnostic catheter and pushing the drive shaft and sheath through the diagnostic catheter until said enlarged distal head is in proximity to the matter within the organ; and
   rotating said drive shaft at high speed relative the coiled wire sheath bearing by rotating a proximal end of the drive shaft not covered by the sheath to effect high speed rotation of the enlarged head to dislodge the matter from said organ.

8. The process of claim 7 wherein in addition to rotating the head at high speed, suction is applied at a proximal end of the diagnostic catheter to remove dislodged matter from the organ either during or after high speed rotation of the rotatable head.

9. The process of claim 7 wherein the opaque dye and saline is injected during high speed rotation of the head and the patient is imaged during said high speed rotation to observe the region of the organ that includes the matter.

10. The process of claim 7 wherein multiple elongated rotatable drives are inserted having differing dimensions during the process.

11. The process of claim 7 wherein as the rotatable head is rotated at high speed it is brought into physical contact with the matter and the elongated catheter is inserted further into the organ to guide the rotatable drive as the rotatable head removes said matter.

12. A catheter system for dislodging material from within an organ comprising:

(a) a drive catheter including a distal tip for engaging the material, a drive shaft coupled to the tip, and an elongated sleeve supporting the drive shaft for rotation relative the elongated sleeve and having an outer surface coated with a synthetic material to facilitate insertion of the drive catheter into a diagnostic catheter, and (b) connector apparatus for directing the drive catheter and a fluid dye through the diagnostic catheter to the region of the material including:

(i) branch connector means having a connector body including first and second input openings in communication with an output opening for routing a fluid dye from one input opening through the output opening and routing the drive catheter from the second input opening through the output opening;

(ii) coupling means for coupling the branch connector means to the diagnostic catheter with the output opening of said connector body opening into the diagnostic catheter for routing said drive catheter and fluid into the diagnostic catheter; and (iii) seal means coupled to the branch connector means for inhibiting the fluid dye entering the first input opening from exiting the second input opening along an outside surface of the elongated sleeve of the drive catheter, the seal means comprising a heat shrinkable plastic tube that sealingly engages the drive catheter sleeve at the second input opening to the connector body while allowing sliding movement to the drive catheter through said connector body to allow positioning of the distal tip relative to the branch connector means.

13. The catheter system of claim 12 wherein the elongated sleeve comprises a tightly coiled wire coated on an outer surface with a synthetic covering.

* * * * *